(12) United States Patent
Blomqvist

(10) Patent No.: US 6,214,837 B1
(45) Date of Patent: Apr. 10, 2001

(54) PHARMACEUTICAL COMPOSITION FOR THE TREATMENT OF SO-CALLED RESTLESS LEGS

(76) Inventor: Göran Blomqvist, Svalnasvagen 19, S-182 63 Djursholm (SE)

( * ) Notice: Subject to any disclaimer, the term of this patent is extended or adjusted under 35 U.S.C. 154(b) by 0 days.

(21) Appl. No.: 09/380,295

(22) PCT Filed: Feb. 3, 1998

(86) PCT No.: PCT/SE98/00199

§ 371 Date: Aug. 31, 1999

§ 102(e) Date: Aug. 31, 1999

(87) PCT Pub. No.: WO98/39005

PCT Pub. Date: Sep. 11, 1998

(30) Foreign Application Priority Data

Mar. 6, 1997 (SE) .................................................. 9700803

(51) Int. Cl.[7] .......................... A61K 31/44; A61K 31/55; A61K 31/445
(52) U.S. Cl. ........................... 514/290; 514/220; 514/315
(58) Field of Search .................... 514/290, 220, 514/315

(56) References Cited

U.S. PATENT DOCUMENTS

| | | | |
|---|---|---|---|
| 3,014,911 | 12/1961 | Engelhardt | 260/293 |
| 4,282,233 | 8/1981 | Vilani | 424/267 |
| 5,759,198 | * 6/1998 | Karell | 607/48 |
| 6,100,274 | * 8/2000 | Kou | 514/290 |

OTHER PUBLICATIONS

"Therapy Consulation", by Walton, et al., Clinical Pharmacy, vol. 10, Jun. 1991, pp. 427–428.
"Randomised Double–Blind Trial of Quinine Sulphate for Nocturnal Leg Cramp", by S. H. Lim,The British Journal of Clinical Practice, vol. 40, No. 11, Nov. 1986, p. 462.
"Cramps, Stiffness and Restless Legs", by Alan M. Whiteley, Practitioner, No. 226, Jun. 1982,pp. 1085–1087.
"Anxietas Tibiarum: Restless Legs and Headache", by M. L. Masterson, Journal of the Kansas Medical Society, No. 81, No. 12, 1980, pp. 566–567, 600.

* cited by examiner

Primary Examiner—Kevin E. Weddington

(74) Attorney, Agent, or Firm—McDermott, Will & Emery

(57) ABSTRACT

A pharmaceutical composition for the treatment of so-called restless legs is disclosed, which composition comprises a combination of: A) quinine, preferably, in the form of a pharmaceutically acceptable acid addition salt thereof; and B) a compound selected from the group consisting of B1) compounds of general formula (I) wherein $R_1$ is hydrogen or a straight or branched alkyl group, having 1–4 carbon atoms, $R_2$ and $R_3$, which are equal or different, each represents hydrogen, a halogen atom, a straight or branched alkyl or alkoxy group having 1–4 carbon atoms, or a trifluoromethyl group, preferably in the form of a pharmaceutically acceptable salt thereof; and B2) compounds of general formula (II) wherein X is hydrogen or a halogen atom, preferably chlorine, and $R_4$ is a methyl, ethyl or phenyl group together with conventional pharmaceutically acceptable carrier substances. The invention also relates to the use of quinine and substance of general formula (I) or (II) for the production of a pharmaceutical composition for the treatment of restless legs and a method of treatment for restless legs in which therapeutic doses of a compound of formula (I) or (II) are administered to the patient in combination with quinine.

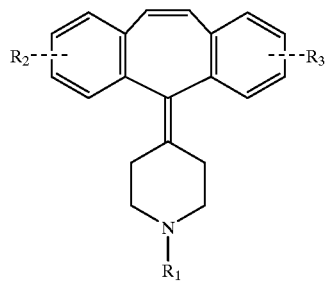

(I)

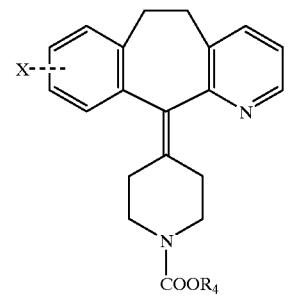

(II)

16 Claims, No Drawings

PHARMACEUTICAL COMPOSITION FOR THE TREATMENT OF SO-CALLED RESTLESS LEGS

The present invention relates to a pharmaceutical composition for the treatment of so-called restless legs, the new use of certain compounds known to act as antihistamines, preferably in combination with quinine, for the preparation of a pharmaceutical composition for the treatment of restless legs, and a new method of treatment of restless legs.

There are several theories about the cause of the affliction experienced as tingling and feelings of crawling in the-lower legs which occurs particularly at night and affects especially older patients. This affliction is termed restless legs. Several methods of treatment have been tried for this affliction, some of which are described in Clinical Pharmacy, Volume 10, June 1991, pages 427–428. No treatment has, however, been particularly successful. This reference describes, among other things, attempts to treat leg cramps by the use of quinine, but does not mention the use of quinine for the treatment of restless legs.

In accordance with the present invention, the surprising observation has been made that certain substances known to be antihistamines can in certain cases give effective relief from the affliction of restless legs, and that a combination of such a substance with quinine gives extraordinary good relief.

Accordingly, the present invention relates to a pharmaceutical composition for the treatment of restless legs, which is characterised in that it comprises a combination of A) quinine, preferably in the form of a pharmaceutically acceptable acid addition salt thereof, and B) a compound selected from the group consisting of B1) compounds of the general formula (I)

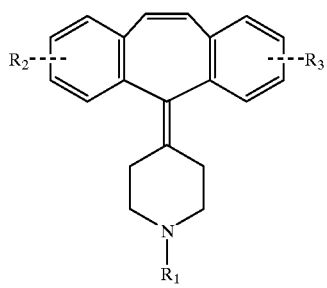

(I)

wherein $R_1$ is hydrogen or a straight or branched alkyl group, having 1–4 carbon atoms, $R_2$ and $R_3$, which are equal or different, each represents hydrogen, a halogen atom, a straight or branched alkyl or alkoxy group having 1–4 carbon atoms, or a trifluoromethyl group, preferably in the form of a pharmaceutically acceptable salt thereof, and B2) compounds of the general formula (II)

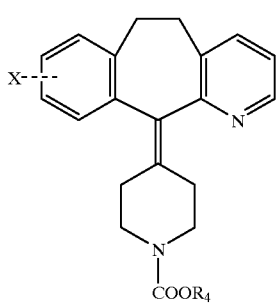

(II)

wherein X is hydrogen or a halogen atom, preferably chlorine, and $R_4$ is a methyl, ethyl or phenyl group together with conventional pharmaceutically acceptable carrier substances.

Compounds of the general formula (I) and their preparation are known, for example from U.S. Pat. No. 3,014,911. The compound most preferred for use in the present invention is cyproheptadine –4-(5H-dibenzo[a,d]cycloheptene-5-ylidene)-1-methyl-piperidine]. This compound is a histamine H1 antagonist which is sold by Merck Sharp and Dohme under the trade name Periactin® with indications acute and chronic allergy, pruritis, and vascular headache.

Compounds of the general formula (II) and processes for their production are known, for example from U.S. Pat. No. 4,282,233. The compound most preferred for use in the present invention is loratadine [ethyl-4-(8-chloro-5,6-dihydro-11H-benzo[5,6]cyclohepta[1,2b]pyridine-11-ylidene)-1-piperidine-carboxylate]. This compound is sold by Schering-Plough AB, Stockholm, Sweden as a histamine H1 antagonist under the trade name Clarityn, with indications allergic rhinitis and conjunctivitis, and histamine mediated pruritis and urticaria.

According to one embodiment of the pharmaceutical composition according to the invention, the two components A) and B) exist together in one and the same pharmaceutical preparation together with conventional pharmaceutically acceptable carriers in a suitable dosage unit form.

According to another embodiment, the pharmaceutical composition according to the invention exists in the form of a kit containing the components A) and B) each in a separate dosage unit. In this case the two components exist separately in tablet form with a known composition for the conventional use of the components in question.

According to a particularly preferred embodiment of the pharmaceutical composition according to the invention said composition consists of a kit with quinine hydrochloride in the form of a tablet containing 50–400 mg, preferably 100–250 mg, quinine hydrochloride, and loratadine in the form of a tablet containing 5–15 mg, preferably 10 mg, loratadine.

According to another aspect of the present invention there is provided the use of quinine for the preparation of a pharmaceutical composition for the treatment of restless legs in combination with a compound with the general formula (I) or (II), as has been defined previously. According to the same aspect, the present invention also relates to the use of a compound with the general formula (I) or (II) as has been defined previously for the preparation of a pharmaceutical composition for the treatment of restless legs in combination with quinine.

According to a preferred embodiment of this use, the quinine exists in the form of quinine hydrochloride, while loratadine is used as a compound with formula (II), the two substances being prepared separately as dosage units.

According to a further aspect of the invention there is provided the use of a compound of the general formula (II) as defined above for the preparation of a pharmaceutical composition for the treatment of restless legs.

According to a still further aspect of the present invention there is provided a method of treatment of restless legs, which method comprises the administration to a patient of a therapeutically effective amount of a compound of formula (I) or (II) as has been defined previously in combination with quinine. According to a preferred embodiment of this method, the quinine is administered in the form of a tablet containing 50–400 mg, preferably 100–250 mg, quinine hydrochloride, and loratadine in the form of a tablet containing 5–15 mg, preferably 10 mg, loratadine.

The present invention also provides a method of treatment of restless legs which method comprises administration to a patient of a therapeutically effective amount of a compound of the general formula (II) as defined above.

The invention will be further illustrated below by a number of examples of the treatment of restless legs using a pharmaceutical composition in accordance with the present invention and using a compound of the general formula (II), with no connection to quinine, respectively.

The following preparations have been used in the experiments: Kinin NM Pharma has been used as quinine. This is marketed by NM Pharma AB, Stockholm, Sweden in the form of tablets containing 100 mg or 250 mg quinine hydrochloride.

Loratadine, in the form of, Clarityn®, has been used as component B) in the composition in accordance with the present invention. This is sold by Schering-Plough AB, Stockholm, Sweden in the form of tablets containing 10 mg loratadine.

EXAMPLE 1

A woman, date of birth 1943, had had prolonged affliction with tingling which she had experienced as essentially disabling. She received 10 mg loratadine twice daily, which had a good effect. Since she occasionally experienced cramp-like sensations, quinine was employed at night, being later increased to 2×100 mg. She noticed, in addition to the disappearance of the cramps, that the tingling was considerably reduced, and essentially disappeared completely with the combination of loratadine and quinine.

EXAMPLE 2

A woman, date of birth 1960, with very severe paresthesia in the legs at night, occasionally also during the day, became totally free of the affliction with loratadine 10 mg and quinine 100 mg daily.

EXAMPLE 3

A woman, date of birth 1936, with severe tingling in the legs mainly at night, with occasional calf cramps, became essentially free of affliction with a combination of loratadine and quinine.

EXAMPLE 4

A woman, date of birth 1924, with over 10 years' affliction with tingling in the legs and, less often, calf cramps, became essentially symptom free with a combination of loratadine 10 mg and quinine 100 mg. The paresthesia returned within ½ to 1 day of discontinuing the treatment and were then just as severe as before the treatment.

EXAMPLE 5

A man, date of birth 1909, with restless legs and occasional calf cramps received 10 mg loratadine and 100 mg quinine, on which both symptoms disappeared. The treatment continued for several months with excellent results, but was discontinued by the patient due to other problems.

EXAMPLE 6

A woman, date of birth 1924, received loratadine 10 mg and quinine 100 mg, and experienced a remarkable improvement, becoming essentially free of affliction from restless legs when the treatment started about 5 months ago.

EXAMPLE 7

A woman, date of birth 1946, who had had both severe tingling and relatively frequent cramps in the legs. Both symptoms disappeared after 1 month's treatment with loratadine 10 mg and quinine 100 mg.

EXAMPLE 8

A woman, date of birth 1910, with paresthesia and aching calves, was treated with loratadine 10 mg and quinine 100 mg. After 3 months' treatment, the patient experienced a certain improvement and is essentially free of affliction with paresthesia while the treatment has had poor effect on the aching calves. No circulation disturbance has been found to explain this.

EXAMPLE 9

A woman, date of birth 1921, with long-standing severe tingling became totally free of affliction with a combination of loratadine 10 mg and quinine 100 mg. The problems returned on attempts to cease treatment.

EXAMPLE 10

A woman, date of birth 1940, with severe tingling for 10 years and occasional cramps in the calves. A combination treatment with 10 mg loratadine and 1–2 100 mg tablets quinine at night gave complete regression of the afflictions after about 1 week. The problems returned if the treatment was ceased.

EXAMPLE 11

A woman, date of birth 1926, with severe tingling in both legs and occasional aches for over 10 years was treated with loratadine 10 mg and quinine 100 mg. The patient has previously been operated for Baker's cysts in the hollow of the knee which were thought to be the cause of her problems. The problems persisted, however. After treatment in accordance with the present invention, the patient experienced a remarkable change, becoming completely free of symptoms in the lower legs with which she had been afflicted for years.

EXAMPLE 12

A woman, date of birth 1914, with tingling since 1986 which had been investigated with magnet tomography and operated to remove spinal stenosis, etc. None of these measures, however, had the slightest effect on her night-time paresthesia. The patient underwent a trial series in which she received 1 tablet quinine 100 mg at night-time for the first week, without effect. Two tablets of 100 mg quinine were applied during the second week, while during the third week 10 mg loratadine on its own was applied, without effect. During the forth week, 2 100 mg tablets quinine were combined with 1 10 mg tablet loratadine. After two days, the paresthesia disappeared, as did the leg aches which she had had for more than 10 years. However, after a few months the tingling started to return around 3 a.m., upon which the earlier dose which had been taken around 11 p.m. was supplemented with a second dose 4–5 hours later. The problems disappeared again, about 30 minutes after the dose.

The following two examples (Examples 13 and 14) show that results on restless legs in certain patients can be achieved by loratadine on its own, and not in combination with quinine.

EXAMPLE 13

A woman, date of birth 1914, who had had long-standing severe bi-lateral affliction with restless legs, received in March 1995 a dosage of 10 mg loratadine in the morning. Within 2 weeks a clear improvement was seen and the patient, who has since been under observation for over a year, is now considered to be essentially free of affliction.

EXAMPLE 14

A woman, date of birth 1947, with tingling on prolonged sitting and hypertonia received 10 mg loratadine daily with very good effect.

What is claimed is:

1. A pharmaceutical composition for the treatment of restless legs, characterized in that it consists of a combination of A) quinine, and
B) a compound selected from the group consisting of
    B1) compounds of the general formula (I)

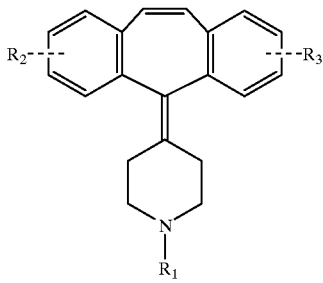

(I)

wherein $R_1$ is hydrogen or a straight or branched alkyl group, having 1–4 carbon atoms,
$R_2$ and $R_3$, which may be equal or different, each represents hydrogen, a halogen atom, a straight or branched alkyl or alkoxy group having 1–4 carbon atoms, or a trifluoromethyl group, and B2) compounds of the general formula (II)

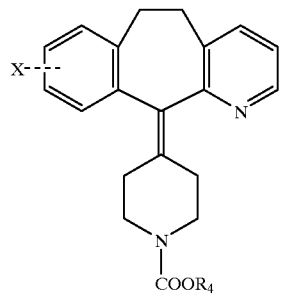

(II)

wherein X is hydrogen or a halogen atom, and $R_4$ is a methyl, ethyl or phenyl group
together with conventional pharmaceutically acceptable carrier substances.

2. The pharmaceutical composition according to claim 1, characterized in that the compound of the general formula (I) is cyproheptadine.

3. The pharmaceutical composition according to claim 1, characterized in that the compound of the general formula (II) is loratadine.

4. The pharmaceutical composition according to claim 1, characterized in that it is a kit of components A) and B), each as separate dosage units.

5. The pharmaceutical composition according to claim 4, characterized in that it is a kit with quinine hydrochloride in tablet form, with tablets containing 50–4000 mg quinine hydrochloride and loratadine in tablet form, each tablet containing 5–15 mg loratadine.

6. The pharmaceutical composition according to claim 1, wherein said halogen atom for said X is chlorine.

7. The pharmaceutical composition according to claim 1, wherein said quinine and said B1 and B2 compounds are in the form of a pharmaceutically acceptable salt thereof.

8. The pharmaceutical composition according to claim 2, wherein said cyproheptadine is in the form of its chloride.

9. The pharmaceutical composition according to claim 5, wherein said quinine hydrochloride containing tablet form contains 100–250 mg of quinine hydrochloride.

10. The pharmaceutical composition according to claim 5, wherein said loratadine containing tablet form contains 10 mg of loratadine.

11. A method of treatment of restless legs which method comprises the administration to a patient of a therapeutically effective dose of a compound of the formula (I) or (II) as defined in claim 1 in combination with quinine.

12. The method according to claim 11, wherein quinine is administered in tablet form, each tablet containing 50–400 mg quinine hydrochloride and loratadine in tablet form, each tablet containing 5–15 mg loratadine.

13. The method according to claim 12, wherein said quinine hydrochloride containing tablet form contains 100–250 mg of quinine hydrochloride.

14. The method according to claim 12, wherein said loratadine containing tablet form contains 10 mg of loratadine.

15. The method according to claim 11, wherein an effective dose of the compound of formula (II) in combination with quinine is administered.

16. The method according to claim 12, wherein said quinine hydrochloride and loratadine are prepared in separate dosage units.

* * * * *